US005623920A

United States Patent [19]
Bryant

[11] Patent Number: 5,623,920
[45] Date of Patent: Apr. 29, 1997

[54] VALVE ASSEMBLIES

[75] Inventor: Andrew M. Bryant, Loughborough, Great Britain

[73] Assignee: Minnesota Mining and Manufacturing Company, St. Paul, Minn.

[21] Appl. No.: 362,520

[22] PCT Filed: Jul. 13, 1993

[86] PCT No.: PCT/GB93/01458

§ 371 Date: Jan. 6, 1995

§ 102(e) Date: Jan. 6, 1995

[87] PCT Pub. No.: WO94/01347

PCT Pub. Date: Jan. 20, 1994

[51] Int. Cl.$^6$ .......................... A61M 11/00; A61M 15/00
[52] U.S. Cl. .................. 128/200.23; 128/200.14; 128/200.19; 128/200.21
[58] Field of Search .................. 128/200.14, 200.23, 128/200.19, 200.21, 200.17; 222/162, 402.13, 402.15

[56] References Cited

U.S. PATENT DOCUMENTS

| | | | |
|---|---|---|---|
| 2,746,796 | 5/1956 | Germain | 299/95 |
| 2,886,217 | 5/1959 | Thiel | 222/394 |
| 3,001,524 | 9/1961 | Maison et al. | 222/402.13 |
| 3,176,887 | 4/1965 | Potapenko et al. | 222/394 |
| 3,283,963 | 11/1966 | Boyer et al. | 222/402.13 |
| 3,565,070 | 2/1971 | Hanson et al. | 128/173 |
| 3,591,059 | 7/1971 | Stearns | 222/402.2 |
| 3,738,542 | 6/1973 | Ruscitti | 222/402.16 |
| 3,900,138 | 8/1975 | Phillips | 222/340 |
| 4,506,803 | 3/1985 | Franklin et al. | 222/402.2 |
| 4,664,107 | 5/1987 | Wass | 128/200.23 |
| 4,819,834 | 4/1989 | Thiel | 222/355 |
| 5,119,806 | 6/1992 | Palson et al. | 128/200.14 |

FOREIGN PATENT DOCUMENTS

| | | | |
|---|---|---|---|
| 0728952 | 3/1966 | Canada | 128/200.23 |
| 0147028A1 | 7/1985 | European Pat. Off. | |
| 0260067A3 | 3/1988 | European Pat. Off. | |
| 0534731A1 | 3/1993 | European Pat. Off. | |
| 2010608 | 10/1970 | Germany. | |
| 864694 | 4/1961 | United Kingdom. | |
| 1200129 | 7/1970 | United Kingdom. | |
| 1246710 | 9/1971 | United Kingdom. | |
| 1287126 | 8/1972 | United Kingdom. | |
| 1311512 | 3/1973 | United Kingdom. | |
| 1310161 | 3/1973 | United Kingdom. | |
| 1336379 | 11/1973 | United Kingdom. | |
| 1370885 | 10/1974 | United Kingdom. | |
| 1445202 | 8/1976 | United Kingdom. | |
| 2086845 | 5/1982 | United Kingdom. | |
| 2004526 | 7/1982 | United Kingdom. | |
| 2077229 | 8/1983 | United Kingdom. | |
| 0191614A2 | 8/1986 | United Kingdom. | |
| 2206099 | 12/1988 | United Kingdom. | |
| 2240930 | 8/1991 | United Kingdom. | |
| WO92/07599 | 5/1992 | WIPO. | |
| WO92/07600 | 5/1992 | WIPO. | |

*Primary Examiner*—Edgar S. Burr
*Assistant Examiner*—V. Srivastava
*Attorney, Agent, or Firm*—Gary L. Griswold; Walter N. Kirn; Dale E. Hulse

[57] ABSTRACT

A valve assembly for a pressurized aerosol container which has a neutral bias. The valve may be of the metered dose type and is preferably springless. Containers equipped with such valves may be employed in breath actuated dispensing devices with simplified mechanisms since it is not necessary to overcome any biasing force within the valve.

20 Claims, 4 Drawing Sheets

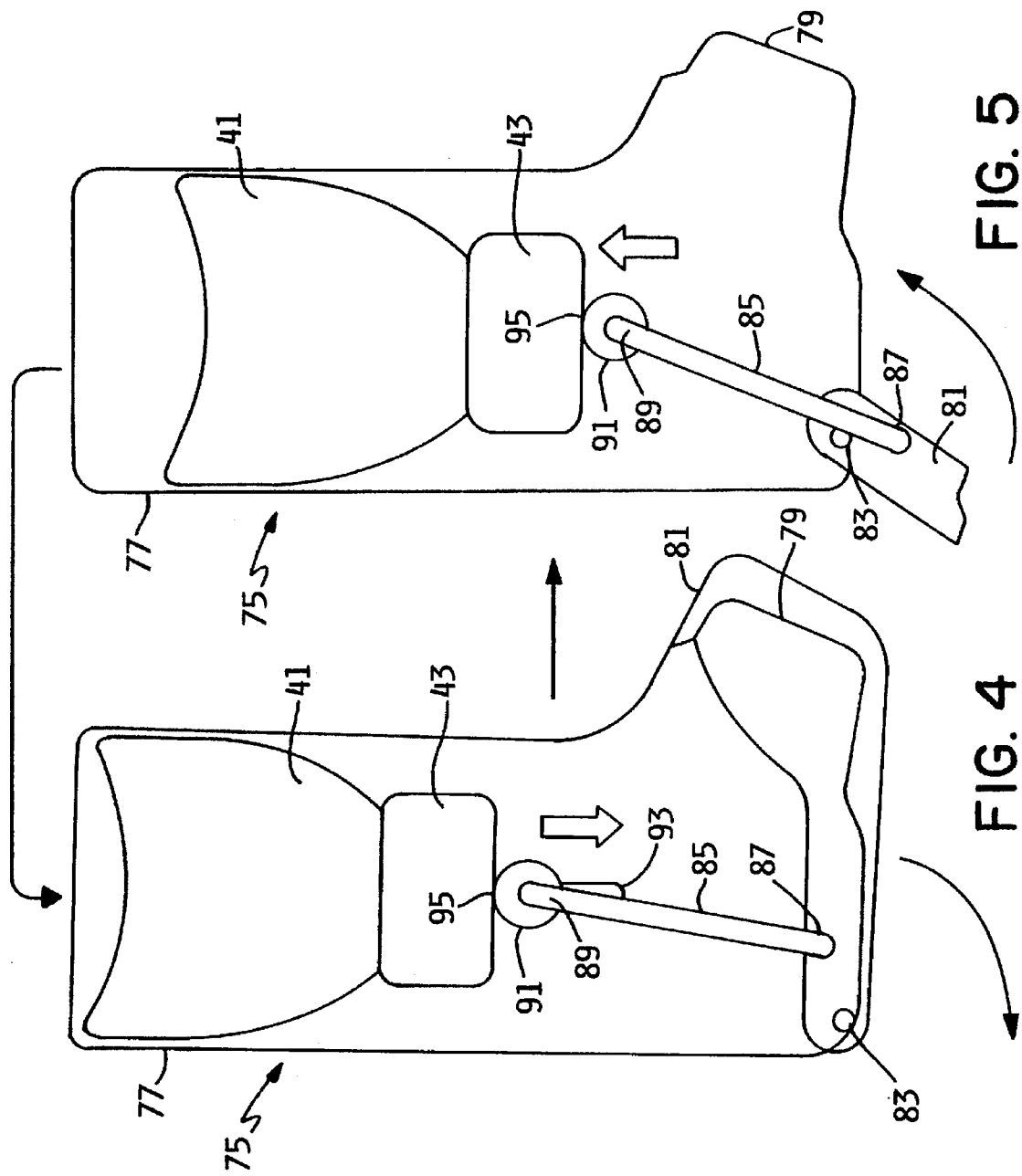

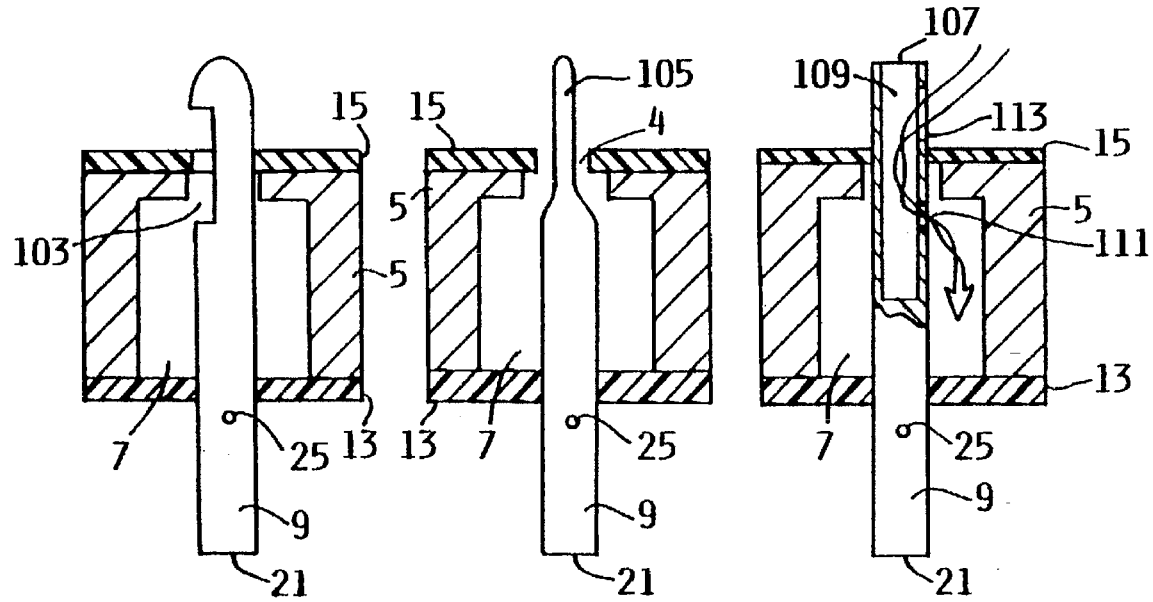
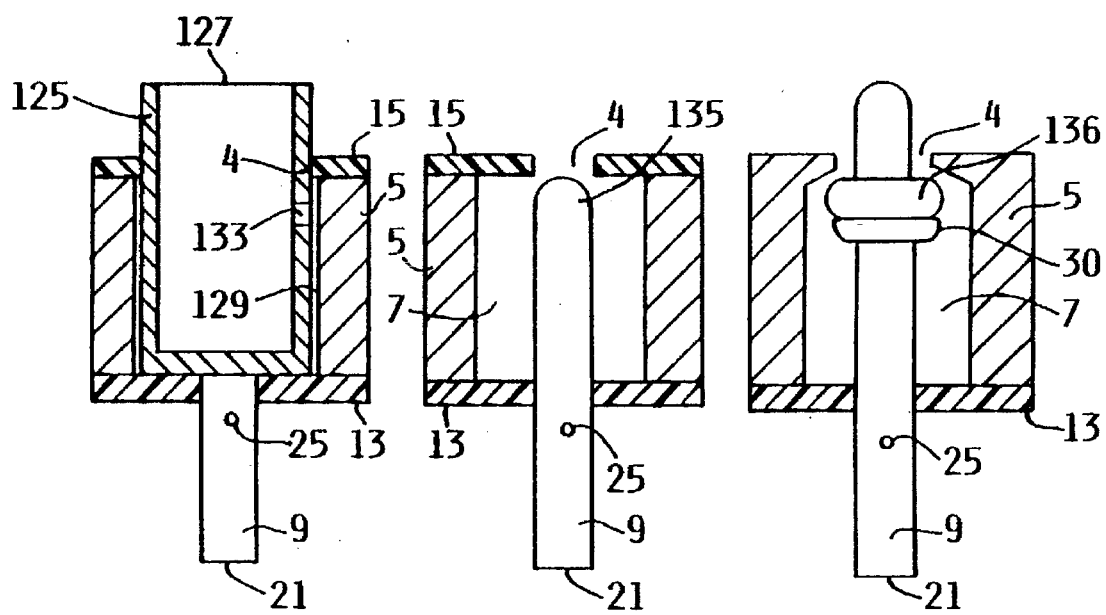

VALVE ASSEMBLIES

FIELD OF THE INVENTION

This invention relates to valve assemblies for pressurised fluid containers such as aerosol containers and in particular to valve assemblies capable of dispensing metered-doses of the contents of an aerosol container.

BACKGROUND

Pressurised fluid containers are in widespread use for dispensing a wide variety of materials including cosmetic materials, e.g., deodorants, body fresheners etc., and domestic cleaning materials, e.g., detergents, polishes, waxes etc. Conventional pressurised fluid containers are provided with a valve assembly for dispensing the container contents comprising a hollow, elongate valve member which is movable relative to the body of the container between an outer closed position and an inner dispensing position. The valve member is biased, usually by a spring, to the outer closed position to prevent the discharge of material from the container when not in use. To actuate the valve assembly, the valve member is depressed inwardly by the user to the dispensing position allowing material to exit from the container.

The use of aerosol devices to administer medicament, such as drugs or other therapeutically active compounds, by inhalation therapy is commonplace, particularly for the treatment of respiratory disorders, such as asthma, where it is important that the amount of material dispensed is a predetermined, accurate volume each time the valve is actuated. The aerosol container is charged with a self-propelling liquid composition containing the medicament dissolved or dispersed therein and provided with a valve assembly capable of dispensing metered amounts of the composition. Examples of such valve assemblies are disclosed in British Patent Nos. 864694, 1287126, 1336379, 2004526, 2077229 and 2086845, European Patent No. 191614 and U.S. Pat. Nos. 2,746,796 and 3,738,542.

Many known metering valve assemblies for pressurised aerosol containers comprise a metering chamber positioned at the outlet of the container which is filled with a fresh dose of the material to be dispensed immediately after the previous dose has been dispensed. This feature is incorporated into the valve assembly to avoid the need to prime the assembly before use. A hollow elongate valve member is arranged for reciprocal movement through the metering chamber between a closed, non-dispensing position where the metering chamber is filled with the material to be dispensed and a dispensing position, in which the metered dose of material is dispensed through the valve member to the outside environment. The valve member is again biased to the closed, non-dispensing position. This arrangement allows the dosage of material dispensed from the aerosol container to be accurately reproduced with each operation of the valve.

In such prior art valve assemblies described above, the elongate valve member is biased to its closed, non-dispensing position, normally under the influence of a spring. Generally, a force must be applied to the valve member to overcome the spring and move the valve member to its dispensing position. There may be certain disadvantages to this arrangement of valve assembly, particularly when fitted to aerosol containers for use with certain types of inhalation devices for dispensing medicament to patients in inhalation therapy.

U.S. Pat. No. 4,506,803 discloses a valve assembly for dispensing metered amounts of material from a main reservoir. The valve assembly includes a metering chamber having a pair of apertures that respectively connect the metering chamber to the main reservoir and to the exterior. A valve seal is mounted within each of the apertures. An additional seal is mounted within the metering chamber, with all the seals in substantial alignment. A slidable valve member comprising dispensing and bypass passages is positioned within and co-operable with the seals. The bypass passage selectively interconnects the main reservoir with the metering chamber and the dispensing passage interconnects the metering chamber with the exterior. The seals selectively co-operate with the two passages as the stem is slidably moved through the metering chamber and the reservoir.

The valve member is biased to a non-dispensing position, in which the dispensing passage is sealingly engaged by one of the chamber seals, by a spring mounted exteriorly of the container so that the bypass passage is positioned within the unfilled metering chamber. The metering chamber is isolated from both the main reservoir and from the exterior of the assembly. The valve member is then depressed inwardly to a charging position in which the inlet aperture of the dispensing passage is sealingly engaged by the additional seal mounted within the metering chamber. Accordingly, the metering chamber and the exterior of the apparatus are isolated. In this position a portion of the bypass passage is moved into the main reservoir, thereby placing the main reservoir and the metering chamber in communication via the bypass passage. This charges the metering chamber with a desired amount of fluid material to be dispensed. The valve member is then released so that it will slide into a dispensing position in which the main reservoir and metering chamber are again isolated from one another; the bypass passage moving into sealing engagement with the other valve seal and back into the metering chamber. During this movement of the stem, the inlet aperture of the dispensing passage first moves out of engagement with the additional seal and then into the metering chamber, whereby material from the metering chamber enters the dispensing passage inlet port, moves through the dispensing passage, and is dispensed through a spray nozzle of the dispensing passage. As the valve member continues to be biased exteriorly, the nozzle continues to dispense a pre-determined amount of the material held within the metering chamber until the dispensing passage inlet port again moves into engagement with the first seal and the assembly again assumes the non-dispensing position.

European Patent Application No. 0260067 discloses a metering valve for a pressurised aerosol container which is configured such that the metering chamber exists only upon actuation of the valve stem to dispense the dosage. Thus, the metering chamber is created, filled with aerosol formulation and emptied during the brief moment the valve stem is depressed and subsequently released by the user to dispense a dose. The valve is biased to its non-dispensing position.

Valves which are biased to the dispensing position are known and are disclosed, for example in GB 1200129, 1246710, 1310161, 1311512, 1370885 and 2240930.

SUMMARY OF THE INVENTION

The present invention seeks to provide a new arrangement of valve assembly for pressurised fluid containers and in particular for pressurised aerosol containers.

According to the present invention there is provided a valve assembly for a pressurised aerosol container in which the valve assembly has a neutral bias. Preferably, the valve assembly is of the metered-dose type.

The valve assemblies of the invention have no net mechanical bias to the dispensing or non-dispensing positions. Preferably the valves are springless. The valve may be provided with means to latch the valve in its closed position. Such neutral biased valves are preferably used in combination with dispensing apparatus incorporating a valve actuation mechanism. The valve actuation mechanism may include biasing means to bias the valve to its open or closed position. Only low bias is required as there is no internal spring in the valve which must be overcome by the valve actuation mechanism. Thus there is little strain on the valve actuation components.

The valve assemblies of the invention may have a wide variety of configurations.

In one embodiment of the present invention there is provided a valve assembly for a pressurised aerosol container, which valve assembly comprises:

a casing adapted to be secured to an aerosol container;

a hollow body secured to the casing and defining a metering chamber having a first opening communicating with the outside environment and a second opening communicating with the interior of the aerosol container;

an elongate valve member sealingly extending through an aperture in the casing and at least the first opening of the metering chamber, which elongate valve member is reciprocally movable between a dispensing position in which there is an open channel through the elongate valve member connecting the metering chamber with the outside environment while the metering chamber is sealed to prevent the passage of material from the interior of the aerosol container to the metering chamber and a closed, non-dispensing position in which the elongate valve member allows the passage of material from the interior of the aerosol container to the metering chamber but prevents the passage of material from the metering chamber to the outside environment, the valve member not being biased to the dispensing or non-dispensing position.

In a further embodiment, the valve assembly comprises a casing adapted to be secured to an aerosol container defining a formulation chamber, the hollow body defining a metering chamber having a first opening communicating with the outside environment and a second opening communicating with the formulation chamber. The elongate valve member comprises an outlet channel communicating with the outside environment and an inlet channel, and is unbiased and reciprocally moveable between:

(i) a dispensing position, in which the outlet channel also communicates with the metering chamber, and in which the valve member is in sealing engagement with the second opening of the metering chamber to prevent the passage of formulation from the formulation chamber to the metering chamber, and (ii) a closed, non-dispensing position, in which the inlet channel of the valve member is in open communication with the formulation chamber and the metering chamber, thereby allowing the passage of formulation from the formulation chamber to the metering chamber, and in which the valve member is in sealing engagement with the first opening in the metering chamber, thereby preventing the passage of formulation from the metering chamber to the outside environment.

In a further embodiment the valve assembly is configured such that the metering chamber only exists upon actuation of the valve stem to dispense the dosage, the valve stem being unbiased. Such valves may have a similar configuration to those disclosed in EP-A-0260067 with suitable modification to remove the biasing means.

According to another aspect of the present invention there is provided a pressurised aerosol container comprising an outlet having a valve assembly as described above for dispensing the material contained therein. Although the valve assemblies may be fitted to most pressurised fluid containers, they are particularly suitable for use with aerosol containers for dispensing medicament in inhalation therapy.

Aerosol containers fitted with a valve assembly of the invention are generally intended to be used in the inverted position, i.e., with the valve assembly held lowermost, for efficient dispensing of the contents held therein. However, the valve assemblies may also be modified for use in an upright position, e.g., by the provision of a dip tube.

Inhalation therapy is an increasingly important method of administering medicaments to a patient. The medicament is formulated into a suitable composition and charged in aerosol container with a suitable propellant. The aerosol container is inserted into an inhalation device comprising a housing adapted to receive the container and a mouthpiece or a port adapted for nasal use through which the patient inhales. The medicament is administered by firing the inhaler, while simultaneously inhaling through the mouthpiece/nasal port. An example of such an inhalation device is commercially available from Minnesota Mining and Manufacturing Company under the trade mark "MEDI-HALER".

The inhaler may also include a breath-actuated mechanism which ensures synchronised dispensing of medicament with inspiration by the patient. An example of a breath-actuated inhaler is commercially available from Minnesota Mining and Manufacturing Company under the trade mark "AUTOHALER" and is disclosed, for example, in European Patent No. 147028.

According to a further aspect of the invention there is provided a portable, hand-held inhaler for administering doses of medicament or other therapeutically active substance to a patient comprising a pressurised container of the invention.

It is with the latter, breath-actuated type of inhalation device that aerosol containers fitted with a valve assembly in accordance with the invention are particularly suitable. Such breath-actuated inhalers generally comprising a housing having a mouthpiece and an air passage therethrough terminating at the mouthpiece, the housing being adapted to receive an aerosol container and having a support block with a socket adapted to receive the valve member of the aerosol container and a through orifice communicating between the socket and the air passage. The inhaler also includes latch means having parts movable between an engaged position in which movement of the container and the support block towards each other (upon the application of a force to bias the container and the support block towards each other) is prevented and a release position in which movement of the container and the support block towards each other (in response to the biasing force) is permitted causing the stem to move to its inner discharge position. The latch means typically comprises a vane mounted on the housing in the air passageway between the orifice and the mouthpiece for movement toward the mouthpiece under the influence of inhalation through the mouthpiece. When a patient inhales through the dispenser, the vane moves towards the mouthpiece from a blocking to a non-blocking position with respect to the passageway to release the latch means.

Conventionally, such breath-actuated inhalers are primed by the patient displacing a cocking lever (typically the mouthpiece cover) immediately prior to their use to cause the container to move against a cocking spring. The cocking spring acts on the base of the aerosol container to urge the container towards the support block. As such, the design of the inhaler is confined somewhat by the need to displace the container relative to the valve member to prime the valve assembly and consequently by the length and overall shape of the container. Furthermore, a not inconsiderable force is required to overcome the biasing means to fire the inhaler. The valves of the invention have considerable benefits for breath-actuated systems, namely:

1. Less force is required to displace the valve member, because there is no valve spring force to overcome.
2. Less force is required to prime the inhaler and the mouthpiece cover may be used for this purpose.
3. The inhaled effort required to trigger the breath actuation mechanism is less.
4. The specifications on components can be more tolerant.
5. A component is eliminated from the conventional valve, making the design simpler.

Aerosol containers fitted with a valve assembly of the invention can also be used with other types of inhalation devices such as those incorporating pneumatic, hydraulic, mechanical, magnetic, electrical and electromechanical means for actuating or resetting the valve or blocking movement or priming actuation of the valve, e.g., as disclosed in our co-pending International Patent Publication Nos. WO92/07599 and WO92/07600.

The elongate valve member generally comprises a discharge orifice through which material can be dispensed from the valve assembly, an outlet passage through which material can pass to the discharge orifice and a transfer port through which material can pass from the metering chamber to the outlet passage. The position of the transfer port on the valve member is arranged such that material from the metering chamber cannot pass through the transfer port in the non-dispensing position, thereby preventing its escape to the outside environment while charging the metering chamber.

While the elongate valve member may be provided with a similar arrangement of orifice, inlet passage and transfer port to allow material to enter the metering chamber from the interior of the container in the non-dispensing position, the outer surface of the inner portion of the valve member may be provided with a filling channel which extends across the second outlet of the metering chamber in the non-dispensing position.

Alternatively, the elongate valve member may be provided with a cutaway or constricted neck portion which extends through the opening of the metering chamber leading to the interior of the container when the valve member is in the closed, non-dispensing position. The relative dimensions of the cutaway/neck portion and the opening of the metering chamber are chosen such that the space defined therebetween allows material from the interior of the aerosol container to freely enter or leave the metering chamber without the flow of material being significantly impeded. In this modified valve, the contents of the aerosol container can, when the container is inverted and the valve member displaced to the non-dispensing position, flow freely into the metering chamber and any gas or vapour that may be in the metering chamber freely exit from the chamber.

Alternatively, the elongate valve member may be completely disengaged from the opening of the metering chamber when the valve member is in the closed, non-dispensing position and the opening suitably dimensioned such that material from the interior of the container can freely enter or leave the metering chamber when the valve member is in the closed, non-dispensing position.

In order to dispense, as near as possible, the entire contents of the aerosol container, thereby avoiding wastage of material, the valve assembly may be provided with a dipcup comprising a second hollow body retained upon and forming a shroud about the first hollow body defining the metering chamber, the shroud extending substantially to the casing and together with the metering chamber defining at least one passage through which material from the aerosol container may pass into the metering tank when the elongate valve member is in the closed, non-dispensing position.

The valve assembly may comprise a pressure filling valve, to enable components of the formulation, maintained in liquid form under pressure, to be introduced under pressure into the aerosol container through the filling valve.

The pressure filling valve may comprise an aperture in the metering chamber communicating with the aerosol container which aperture is adjacent to the casing and is covered by a sealing member which prevents the passage of material from the interior of the aerosol container to the metering chamber but allows passage of material from the interior of the metering chamber to the aerosol container when there is sufficient pressure difference between the metering chamber and aerosol container. To prevent permanent displacement of the sealing member from the aperture when filling the container, the valve assembly preferably comprises a shroud as defined above but shaped so as to cover the sealing member and to allow it limited movement, thereby facilitating pressure filling but preventing permanent displacement of the sealing member.

BRIEF DESCRIPTION OF THE DRAWINGS

The invention will now be described by way of example with reference to the accompanying, non-limiting drawings in which:

FIGS. 2 and 3 illustrate the actuation of a valve assembly in accordance with the invention in which FIG. 2 is a sectional view of the valve assembly in the closed, non-dispensing position and FIG. 3 is a sectional view of the same valve assembly in the dispensing position;

FIGS. 4 and 5 represent a schematic illustration of a priming mechanism suitable for use with either a manual or breath actuated inhaler.

FIGS. 6 to 12 are sectional views of further embodiments of valve assemblies in accordance with the invention.

DETAILED DESCRIPTION

Figure 1:
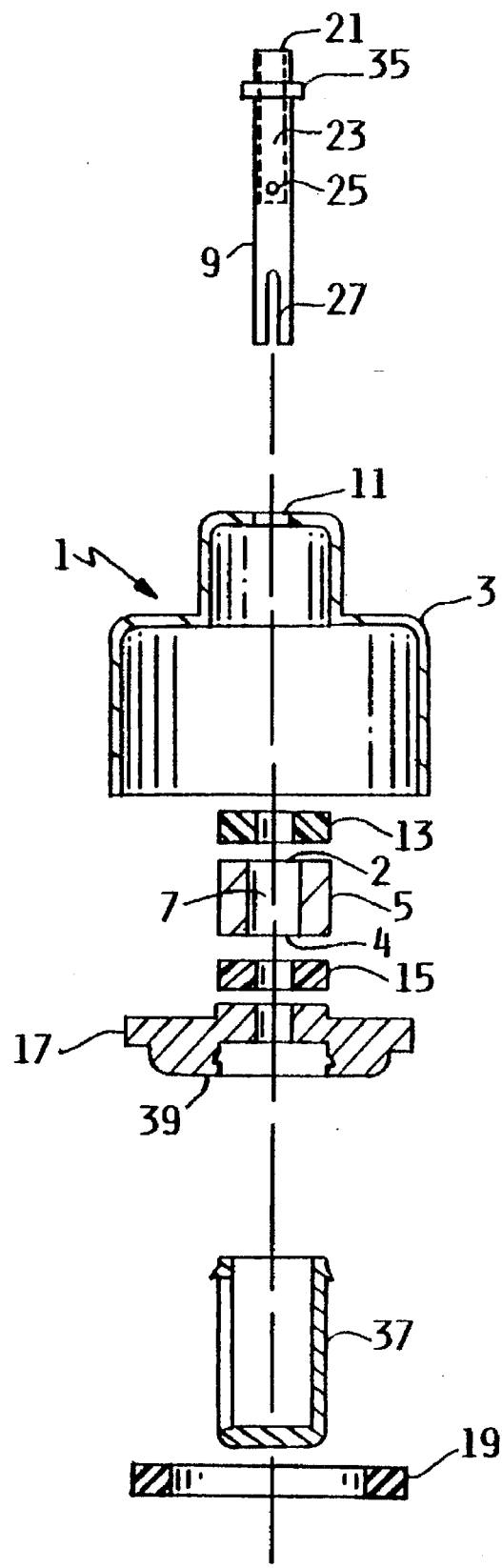
FIG. 1 is an exploded sectional view of a valve assembly in accordance with the invention.

Referring to FIG. 1, the valve assembly (1) comprises a casing (3) adapted to form the closure cap or ferrule of an aerosol container (not shown), a hollow body (5) which defines a metering chamber (7) having an opening at either end thereof (2 and 4) and an elongate, longitudinally reciprocable valve member (9) which extends centrally through an aperture (11) in the casing (3) and each opening (2 and 4) of the metering chamber (7). The innermost end of the valve member (9) sealingly extends through one opening (4) of the metering chamber (7) into the interior of the aerosol container when the valve assembly is fitted, e.g., by crimping, swaging, rolling etc., onto the container. The outermost end of the valve member (9) sealingly extends through the other outlet (2) of the metering chamber (7) and the aperture (11) of the casing (3) to the outside environment. Outer and inner sealing gaskets (13 and 15 respectively) are provided at each end of the hollow body (5) to prevent the escape of material from the metering chamber (7). A base member (17) is provided to secure the hollow body (5) in position. The valve assembly (1) is crimped over the neck of an aerosol container (not shown) with the provision of a sealing gasket (19) to provide a gas tight seal between the casing (3) and the container.

The valve member (9) is movable between an outer non-dispensing position (shown in FIG. 2) and an inner dispensing position (shown in FIG. 3) and includes at its outermost end a discharge orifice (21) which communicates via an outlet passage (23) with a transfer port (25). The valve member (9) is arranged such that the transfer port (25) is disposed inside the metering chamber (7) when the valve member (9) is in the dispensing position, thereby allowing material to pass from the metering chamber (7) to the outside environment and outside of the casing (3) when the valve member (9) is in the non-dispensing position. The valve member (9) includes at its innermost end, on the outer surface thereof, a filling channel (27) which allows material contained in the aerosol container to enter the metering chamber (7) but only when the valve member (9) is in the closed, non-dispensing position.

The outermost end of the valve member (9) is advantageously provided with an annular flange (35) to prevent the valve member (9) from being pulled into the valve assembly (1) and/or a gripping portion. The valve assembly (1) is optionally provided with a guiding shroud which in the embodiment shown comprises a plurality of longitudinal ribs (37). The guiding shroud clips into a complementary recess (39) in the base member (17) to ensure smooth movement of the valve member (9) and to act as a stop for inward movement of valve member (9).

Figure 2:
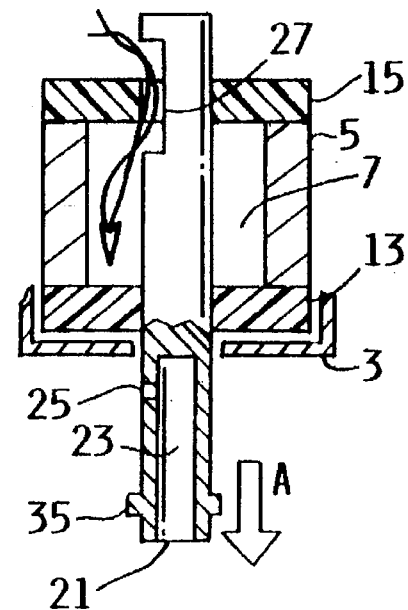
Figure 3:
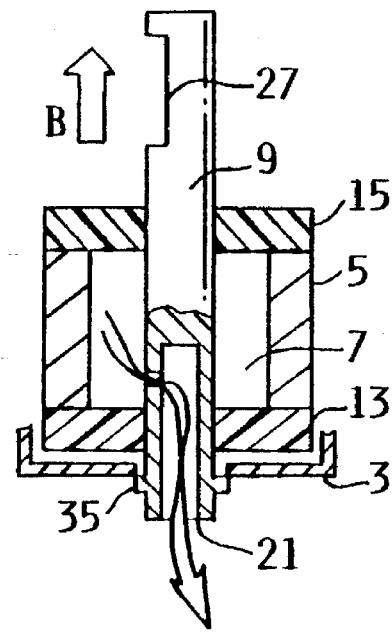

FIGS. 2 and 3 illustrate schematically the working stroke of a slightly modified valve assembly to that shown in FIG. 1. The base member (17) and guiding shroud have been omitted. The valve assembly (1) has also been inverted.

Referring to FIG. 2, the metering chamber (7) is charged by outwardly displacing the valve member (9) in the direction indicated by the arrow marked 'A' to the closed, non-dispensing position. This allows material from the container to enter and fill the metering chamber (7) via filling channel (27). The transfer port (25) is, in turn, positioned outside of the casing (3), thereby preventing the escape of material held in the metering chamber (7) to the outside environment.

When a displacing force is applied to the valve member (9) it urges it in the direction indicated by the solid arrow marked 'B' to the dispensing position. In this position, the transfer port (25) is located within the metering chamber (7) allowing the material held therein to exit through the outlet passage (23) to the discharge orifice (21). The filling groove (27) is, in turn, located entirely within the aerosol container, thereby sealing the metering chamber (7) against the entry of additional material until the next actuation of the valve assembly (1).

Breath-actuated metered-dose inhalation devices of the type disclosed in European Patent No. 147028 but adapted for use with an aerosol container having a valve assembly in accordance with the invention are typically provided with a movable cover which is displaced by the patient to allow him or her access to the mouthpiece. The act of opening and closing the cover may conveniently be used to prime the inhalation device by effecting displacement of the body portion of the aerosol container.

One such arrangement is shown in FIGS. 4 and 5 for an inhalation device (75) comprising a housing (77) adapted to receive an aerosol container and having a mouthpiece (79) and a cover (81) pivotally mounted at (83) which is movable between a closed position shown in FIG. 4 and an open position shown in FIG. 5 which allows the patient access to the mouthpiece (79). The internal components of the inhaler, namely the support block, the breath-actuation mechanism, the top spring and the valve assembly of the aerosol container have been omitted to more clearly illustrate the priming mechanism. A linking member (85) pivotally mounted at one end (87) to the cover (81) and at the opposite end (89) to a roller (91) is provided to translate movement of the cover (81) into movement of the body portion (41) of the aerosol container. The roller (91) is slidably mounted in a guide slot (93) formed in the inner wall of the housing (77). The housing is desirably provided with two such linking members (85) one arranged either side of the housing (77) to facilitate movement of the aerosol container.

After the patient has used the inhalation device (75), the cover (81) is returned by the patient to protect the device against contamination by dirt, moisture ingress etc. Closing the cover (81) drives the roller (91) from the position shown in FIG. 5 to that shown in FIG. 4 with the upper surface (95) of the roller (91) engaging the ferrule (43) of the aerosol container, thereby displacing the body portion (41) of the container against the top spring (not shown) and relative to the valve member (not shown) and charging the metering chamber (also not shown) of the valve assembly with the next dose of medicament.

The extent of roller (91) displacement and hence lift imparted to the aerosol container is proportional to the extent of closing of the cover (81). In use, the inhalation device (75) is held in the hand such that the housing (77) approximates to the vertical.

When the next dose falls due, the patient re-opens the cover (81) causing the roller (91) and body portion (41) of the container to return to the position shown in FIG. 5. However, while movement of the former continues unhindered, the ferrule (43) of the aerosol container is engaged by the interrupter element (not shown) of the breath actuation mechanism as described above, thereby arresting movement of the container and preventing the dose of medicament held in the metering chamber from being dispensed until the patient inhales through the mouthpiece (79). This priming mechanism could also be used in non-breath-actuated inhalers to reset the valve.

Each of FIGS. 6 to 12 illustrates an alternative arrangement of valve assembly in accordance with the invention. Each valve assembly is shown in the closed, non-dispensing position with the valve member displaced fully outwards.

Referring to FIG. 6, the innermost end of the valve member (9) is provided with a cutaway (103) instead of a filling groove to allow material (from the aerosol container—not shown) to enter the metering chamber (7) when the valve member (9) is in its closed, non-dispensing position. The larger dimensions of the cutaway (103) allows material to enter (or leave) the metering chamber (7) under the action of gravity without the flow of material being significantly impeded.

Referring to FIG. 7 the innermost end of the valve member (9) is provided with a neck portion (105) of smaller cross-section than the remainder of the valve member (9)

which, when the valve member (9) is in the closed, non-dispensing position, extends through the opening (4) of the metering chamber (7). The relative dimensions of the neck portion (105) and the opening (4) are such that the space defined therebetween allows material to freely enter or leave the metering chamber (7) under the action of gravity without the flow of material being significantly impeded and any gas or vapour that may be in the metering chamber (7) to exit therefrom.

Referring to FIG. 8, the innermost end of the valve member (9) is provided with an inlet orifice (107) which communicates via an inlet passage (109) with a transfer port (111). The valve member (9) is arranged such that the transfer port (111) is disposed inside the metering chamber (7) when the valve member (9) is in the closed, non-dispensing position, thereby allowing material to pass from the aerosol container (not shown) to the metering chamber (7), and outside the metering chamber when the valve member (9) is in the dispensing position (not shown). The valve member (9) is desirably provided with a side orifice (113) which allows substantially all the entire contents of the container to be dispensed therefrom.

Figure 9:
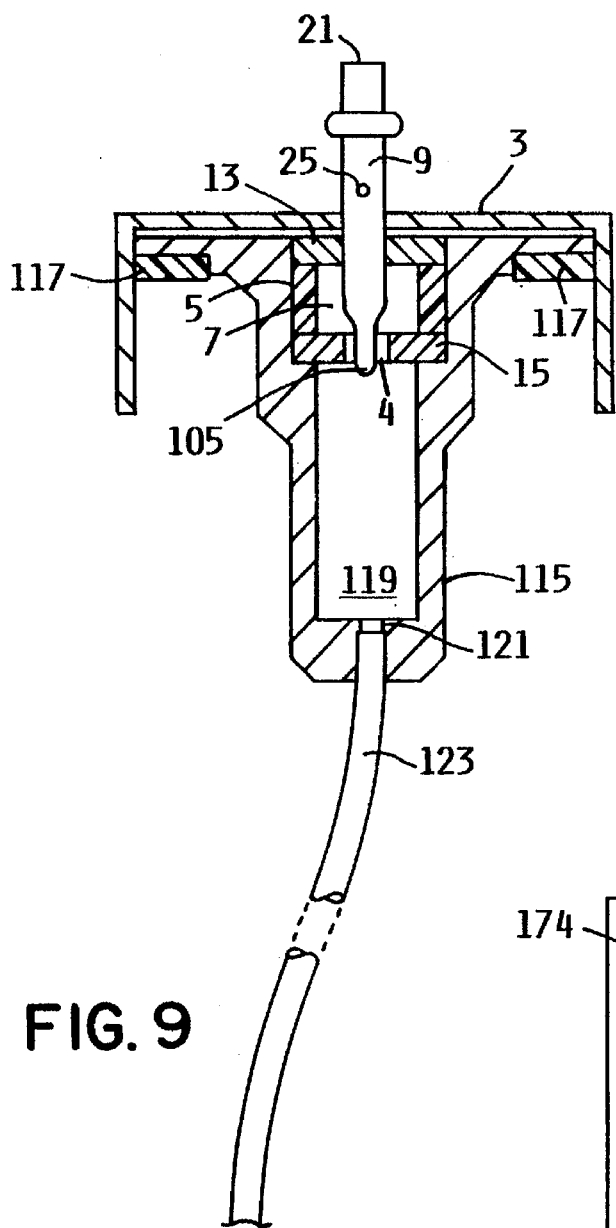

Referring to FIG. 9, the valve assembly comprises an inner housing (115) which together with a sealing gasket (117) surrounds and secures the valve assembly in position. The inner housing (115) defines a chamber (119) which communicates with the opening in the inner sealing gasket (15) leading into the metering chamber (7), having at one end thereof an inlet passage (121) provided with a dip tube (123). The provision of a dip tube (123) allows an aerosol container fitted with such an assembly to be used in a substantially upright position. Material may pass from the chamber (119) to the metering chamber (7) through the opening (4) formed between the neck portion (105) of the stem and the sealing gasket (15).

Referring to FIG. 10, the valve member (9) is formed with a tubular portion (125) sealingly extending through an opening (4) in the inner sealing gasket (15). One end of the tubular portion (125) is provided with an opening (127) communicating with the interior of the aerosol container such that when the aerosol container is inverted, the tubular portion (125) is filled with material from the container. The tubular portion (125) of the valve member (9) has a close but not exact fit within the hollow body (5) to define a channel (129) running therebetween.

The valve member (9) is arranged such that the transfer port (133) of the tubular portion (125) is disposed inside the hollow body (5) in the closed, non-dispensing position, allowing material to pass into the space vacated by the tubular portion (125) as the valve member moves to the dispensing position, but disposed outside of the hollow body (5) in the dispensing position, thereby allowing the material contained therein to exit to the outside environment via transfer port (25) as described above.

FIGS. 11 and 12 illustrate valve assemblies where the valve member (9) is completely disengaged from the opening (4) of the metering chamber (7) when the valve member (9) is in the closed, non-dispensing position. In FIG. 11 the opening (4) is sealed by the end of stem (135) filling the opening and in FIG. 12 the end of the stem is provided with a deformable annular ring (136) which plugs the opening (4) when the valve member (9) is depressed to prevent additional material entering the chamber (7) from the aerosol container (not shown). In this manner, the opening (4) may be dimensioned to allow material to move freely into the metering chamber (7) as described previously for the valve assembly shown in FIG. 7. An annular ring (30) is provided on the valve member (9) to support the deformable annular ring (136).

Figure 13:
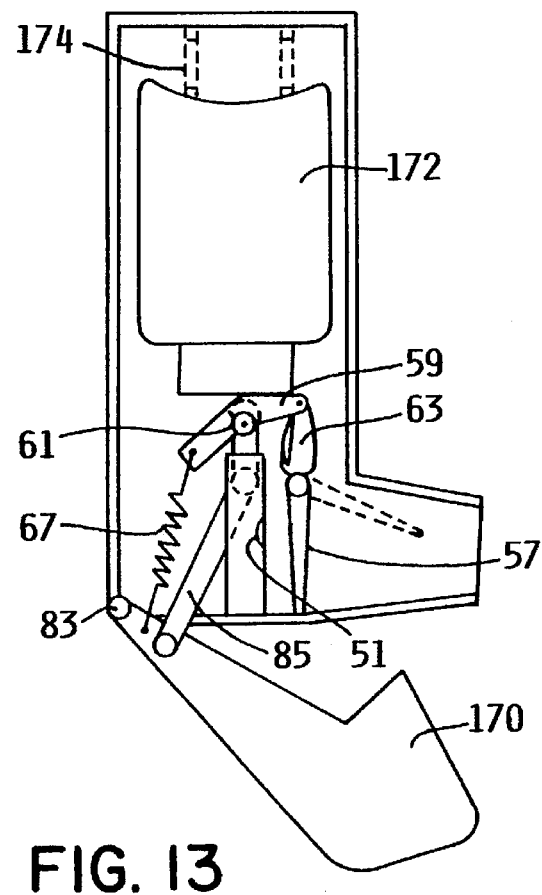
FIG. 13 represents a sectional view of a breath actuated inhaler incorporating a valve of the invention.

FIG. 13 illustrates an inhaler of the invention including a breath-actuated mechanism comprising a vane (57), catch (63), and rocker (59).

When the patient inhales operating the breath-actuating mechanism, the aerosol container (172) is moved under the influence of the spring (174) firing the valve.

I claim:

1. A valve assembly for a pressurised aerosol container comprising:

a casing capable of being secured to an aerosol container;

a hollow body secured to the casing and defining a metering chamber having a first opening communicating with the outside environment and a second opening communicating with the interior of the aerosol container; and an elongate valve member sealingly extending through an aperture in the casing and at least the first opening of the metering chamber, which elongate valve member is reciprocally movable between a dispensing position in which there is an outlet channel through the elongate valve member connecting the metering chamber with the outside environment and the metering chamber is sealed to prevent the passage of material from the interior of the aerosol container to the metering chamber and a closed, non-dispensing position in which the elongate valve member allows the passage of material from the interior of the aerosol container to the metering chamber but prevents the passage of material from the metering chamber to the outside environment;

the elongate valve member having no net mechanical bias to the dispensing or non-dispensing positions.

2. A valve assembly as claimed in claim 1 wherein the aerosol container defines a formulation chamber, wherein the second opening communicates with the formulation chamber, and wherein the elongate valve member further comprises an inlet channel, which elongate valve member is reciprocally moveable between:

(i) the dispensing position, in which the outlet channel communicates with the metering chamber, and in which the elongate valve member is in sealing engagement with the second opening of the metering chamber to prevent the passage of formulation from the formulation chamber to the metering chamber, and (ii) the closed, non-dispensing position, in which the inlet channel of the elongate valve member is in open communication with the formulation chamber and the metering chamber, thereby allowing the passage of formulation from the formulation chamber to the metering chamber, and in which the valve member is in sealing engagement with the first opening in the metering chamber, thereby preventing the passage of formulation from the metering chamber to the outside environment.

3. A valve assembly for a pressurised aerosol container as claimed in claim 2 in which the elongate valve member comprises a discharge orifice through which material can be dispensed from the valve assembly, an outlet passage through which material can pass to the discharge orifice and a transfer port through which material can pass from the metering chamber to the outlet passage, the elongate valve member being arranged such that in the non-dispensing position material cannot pass through the transfer port from the metering chamber.

4. A valve assembly for a pressurised aerosol container as claimed in claim 1 in which the elongate valve member comprises a filling channel disposed on the outer surface thereof along which material can pass from the interior of the aerosol container to the metering chamber, the elongate valve member being arranged such that in the dispensing position material cannot pass along the filling channel to the metering chamber.

5. A valve assembly for a pressurised aerosol container as claimed in claim 1 further comprising a second hollow body retained upon and forming a shroud about the first hollow body, the shroud extending substantially to the casing, and in which the shroud and first hollow body define at least one passage through which material from the interior of the aerosol container may pass into the metering chamber when the elongate valve member is in the closed, non-dispensing position.

6. A valve assembly for a pressurised aerosol container as claimed in claim 5 in which the metering chamber has a pressure filling valve comprising an aperture in the metering chamber communicating with the interior of the aerosol container, which aperture is adjacent to the casing and is covered by a sealing member which prevents the passage of material from the interior of the aerosol container to the metering chamber but allows passage of material from the metering chamber to the interior of the aerosol container when there is sufficient pressure difference between the metering chamber and aerosol container, the shroud being shaped to cover the sealing member of the pressure filling valve to allow limited movement thereof to facilitate pressure filling but preventing permanent displacement of the sealing member from the aperture in the metering chamber.

7. A valve assembly for a pressurised aerosol container as claimed in claim 1 in which the elongate valve member comprises a cutaway portion which extends through the second opening of the metering chamber when the elongate valve member is in the closed, non-dispensing position, and in which the relative dimensions of the cutaway portion and the second opening are such that the space defined therebetween allows material from the interior of the aerosol container to freely enter or leave the metering chamber.

8. A valve assembly for a pressurised aerosol container as claimed in claim 1 in which the elongate valve member is completely disengaged from the second opening of the metering chamber when the valve member is in the closed, non-dispensing position and the second opening is dimensioned such that when the elongate valve member is in the closed position and the elongate valve member is completely disengaged from the second opening, material from the interior of the container can freely enter or leave the metering chamber.

9. A valve assembly as claimed in claim 1 wherein the elongate valve member is configured so as to occupy substantially the entire volume of the metering chamber when the elongate valve member is in the rest position such that the metering chamber exists only upon actuation of the elongate valve member to dispense a metered dose.

10. A pressurised aerosol container comprising an outlet having a valve assembly as claimed in claim 1 for dispensing the contents thereof.

11. A pressurised aerosol container as claimed in claim 10 in which the container is charged with a self-propelling liquid composition having dissolved or dispensed therein a medicament or such other therapeutically active substance.

12. A portable, hand-held inhaler for administering doses of medicament or other therapeutically active substance to a patient comprising a pressurised aerosol container as claimed in claim 10.

13. An inhaler as claimed in claim 12 further comprising a breath-actuation mechanism to synchronise dispensing of the medicament or such other substance with inspiration by the patient.

14. An inhaler as claimed in claim 13 wherein said breath-actuation mechanism includes a spring, external to the valve assembly, which spring causes the elongate valve member to move from its non-dispensing position to its dispensing position when said breath-actuation mechanism is triggered.

15. An inhaler as claimed in claim 14 wherein said spring is positioned above said pressurised aerosol container.

16. An inhaler as claimed in claim 14 wherein said valve assembly itself is springless.

17. An inhaler as claimed in claim 14 wherein the elongate valve member moves inwardly from its non-dispensing position towards its dispensing position.

18. A valve assembly as claimed in claim 1 wherein said valve assembly is springless.

19. A valve assembly as claimed in claim 1 wherein the elongate valve member moves inwardly from its non-dispensing position towards its dispensing position.

20. A valve assembly for a pressurised aerosol container as claimed in claim 1 in which the elongate valve member comprises a constricted neck portion which extends through the second opening of the metering chamber when the elongate valve member is in the closed, non-dispensing position, and in which the relative dimensions of the constricted neck portion and the second opening are such that the space defined therebetween allows material from the interior of the aerosol container to freely enter or leave the metering chamber.

* * * * *